(12) United States Patent
Oma et al.

(10) Patent No.: US 7,859,664 B2
(45) Date of Patent: Dec. 28, 2010

(54) PLURALITY OF SAMPLES AND METHOD FOR SELECTING A TARGET SAMPLE THEREFROM

(75) Inventors: Peter Oma, Ottawa (CA); Deepak Kumar Sharma, Ottawa (CA)

(73) Assignee: Brightwell Technologies Inc., Ottawa (CA)

( * ) Notice: Subject to any disclaimer, the term of this patent is extended or adjusted under 35 U.S.C. 154(b) by 301 days.

(21) Appl. No.: 12/209,260

(22) Filed: Sep. 12, 2008

(65) Prior Publication Data

US 2009/0073437 A1     Mar. 19, 2009

Related U.S. Application Data

(60) Provisional application No. 60/971,935, filed on Sep. 13, 2007.

(51) Int. Cl.
*G01N 15/02* (2006.01)
(52) U.S. Cl. ............... 356/335; 356/237.1; 356/243.8; 356/128
(58) Field of Classification Search ......... 356/335–336, 356/237.1–243.8, 128
See application file for complete search history.

(56) References Cited

U.S. PATENT DOCUMENTS

| | | | |
|---|---|---|---|
| 4,331,862 A | | 5/1982 | Ryan ........................... 377/29 |
| 5,286,452 A | * | 2/1994 | Hansen ........................ 422/73 |
| 5,438,408 A | * | 8/1995 | Weichert et al. ............. 356/336 |
| 5,818,583 A | * | 10/1998 | Sevick-Muraca et al. ..... 356/336 |
| 6,475,800 B1 | | 11/2002 | Hazen et al. .................... 436/8 |
| 6,521,729 B1 | | 2/2003 | Zelmanovic et al. ......... 526/245 |
| 6,542,833 B1 | | 4/2003 | Nygaard ....................... 702/46 |
| 7,187,441 B1 | * | 3/2007 | Sevick-Muraca et al. ..... 356/336 |
| 7,320,823 B2 | * | 1/2008 | Kitahara et al. ............. 428/212 |
| 2006/0033909 A1 | | 2/2006 | Bowers et al. ........... 356/243.6 |

* cited by examiner

*Primary Examiner*—Tarifur R. Chowdhury
*Assistant Examiner*—Isiaka O Akanbi
(74) *Attorney, Agent, or Firm*—Teitelbaum & MacLean; Neil Teitelbaum; Doug MacLean

(57) ABSTRACT

The present invention provides a plurality of samples, each of which includes particles of a predetermined particle dimension, within narrow predetermined limits, dispersed in a carrier at a predetermined particle concentration. The predetermined particle dimension and the predetermined particle concentration are the same for each sample. However, advantageously, each sample has a different predetermined ratio of a value of an optical property of the particles to a value of the same optical property of the carrier. The present invention also provides a method for selecting a target sample from the plurality of samples to assess the measurement accuracy or the detection sensitivity of an optical particle analyzer as the predetermined ratio approaches 1.

18 Claims, 5 Drawing Sheets

PLURALITY OF SAMPLES AND METHOD FOR SELECTING A TARGET SAMPLE THEREFROM

CROSS-REFERENCE TO RELATED APPLICATIONS

The present invention claims priority from U.S. Patent Application No. 60/971,935, filed on Sep. 13, 2007, which is incorporated herein by reference.

TECHNICAL FIELD OF THE INVENTION

The present invention relates to particle standards for optical particle analyzers, and in particular, to a plurality of samples and a method for selecting a target sample therefrom with an optical particle analyzer.

BACKGROUND OF THE INVENTION

Optical particle analyzers are frequently used in pharmaceutical, environmental, life-science, and materials-science applications to measure particle dimensions and particle concentrations of samples including particles dispersed in a carrier. The validity of such measurements is dependent on the measurement accuracy and the detection sensitivity of the optical particle analyzer. Measurement accuracy is the ability of the optical particle analyzer to measure particle dimensions accurately. Detection sensitivity is the ability of the optical particle analyzer to measure particle concentrations accurately.

The detection sensitivity and the measurement accuracy of an optical particle analyzer are, typically, assessed using a particle standard. A conventional particle standard is a sample including particles of a predetermined particle dimension, within narrow predetermined limits, dispersed in a carrier at a predetermined particle concentration. In most instances, the carrier is a fluid, usually water, as described in U.S. Pat. No. 6,542,833 to Nygaard, issued on Apr. 1, 2003, and in U.S. Pat. No. 4,331,862 to Ryan, issued on May 25, 1982, for example; however, in some instances, the carrier is a solid plate, as described in U.S. Patent Application Publication No. 2006/0033909 to Bowers, et al., published on Feb. 16, 2006. The predetermined particle dimension and the predetermined particle concentration of the particle standard are, generally, matched to the particle dimension and the particle concentration, respectively, of a sample under study. Furthermore, a value of an optical property of the particles and/or a value of an optical property of the carrier may also be matched to those of the sample under study, as described in U.S. Pat. No. 6,521,729 to Zelmanovic, et al., issued on Feb. 18, 2003, and in U.S. Pat. No. 6,475,800 to Hazen, et al., issued on Nov. 5, 2002.

The particle dimension of the particle standard is measured with the optical particle analyzer, and the measured particle dimension is compared to the predetermined particle dimension to determine the measurement accuracy of the optical particle analyzer for that particle standard. Similarly, the particle concentration of the particle standard is measured with the optical particle analyzer, and the measured particle concentration is compared to the predetermined particle concentration to determine the detection sensitivity of the optical particle analyzer for that particle standard.

The measurement of particle dimensions and particle concentrations of samples including particles and a carrier having similar values of an optical property poses particular challenges. Examples of such samples include protein drug formulations and cell-culture samples. As the value of an optical property, such as refractive index or a transmission property, of the particles approaches that of the carrier, it becomes increasingly difficult for the optical particle analyzer to distinguish the particles from the carrier. As a result, the optical particle analyzer is susceptible to measurement errors. For example, if the contrast between the particles and the carrier is insufficient, the outer edges of the particles may effectively disappear to the detector of the optical particle analyzer, leading to a measured particle dimension that is smaller than the actual particle dimension. Furthermore, some particles may not be detected at all, leading to a measured particle concentration that is lower than the actual particle concentration.

Thus, it would be desirable to assess the measurement accuracy and the detection sensitivity of an optical particle analyzer for samples in which the particles and the carrier have similar values of an optical property. Such an assessment would permit minimum instrument specifications to be established, instrument performance to be compared, standardized, and verified, and advances in instrument technology to be quantified. Unfortunately, a set of particle standards necessary for such an assessment does not currently exist.

An object of the present invention is to provide a plurality of samples, each of which includes particles dispersed in a carrier, to be used as a set of particle standards for assessment of the measurement accuracy or the detection sensitivity of an optical particle analyzer as a value of an optical property of the particles approaches that of the carrier. The present invention also provides a method of using the plurality of samples for such an assessment.

SUMMARY OF THE INVENTION

Accordingly, the present invention relates to a plurality of samples for selecting a target sample from the plurality of samples, each sample comprising: a carrier; and particles of a predetermined particle dimension, within narrow predetermined limits, dispersed in the carrier at a predetermined particle concentration; wherein the predetermined particle dimension and the predetermined particle concentration are the same for each sample; wherein each sample has a predetermined ratio of a value of an optical property of the particles to a value of the same optical property of the carrier; and wherein the predetermined ratio is different for each sample.

Another aspect of the present invention relates to a method for selecting a target sample from a plurality of samples with an optical particle analyzer, comprising: providing the plurality of samples; wherein each sample comprises a carrier, and particles of a predetermined particle dimension, within narrow predetermined limits, dispersed in the carrier at a predetermined particle concentration; wherein the predetermined particle dimension and the predetermined particle concentration are the same for each sample; wherein each sample has a predetermined ratio of a value of an optical property of the particles to a value of the same optical property of the carrier; and wherein the predetermined ratio is different for each sample; measuring the particle dimension or the particle concentration of each sample with the optical particle analyzer to provide a measured particle dimension or a measured particle concentration, respectively, for each sample; comparing the measured particle dimension to the predetermined particle dimension or the measured particle concentration to the predetermined particle concentration to determine a measurement accuracy or a detection sensitivity, respectively, for each sample; and selecting the target sample for which the predetermined ratio is closest to 1 and for which the measurement accuracy or the detection sensitivity is equal to or better than a desired measurement accuracy or a desired detection sensitivity, respectively.

BRIEF DESCRIPTION OF THE DRAWINGS

The present invention will be described in greater detail with reference to the accompanying drawings, which relate to exemplary, preferred embodiments thereof, wherein.

DETAILED DESCRIPTION OF THE INVENTION

Figure 1:
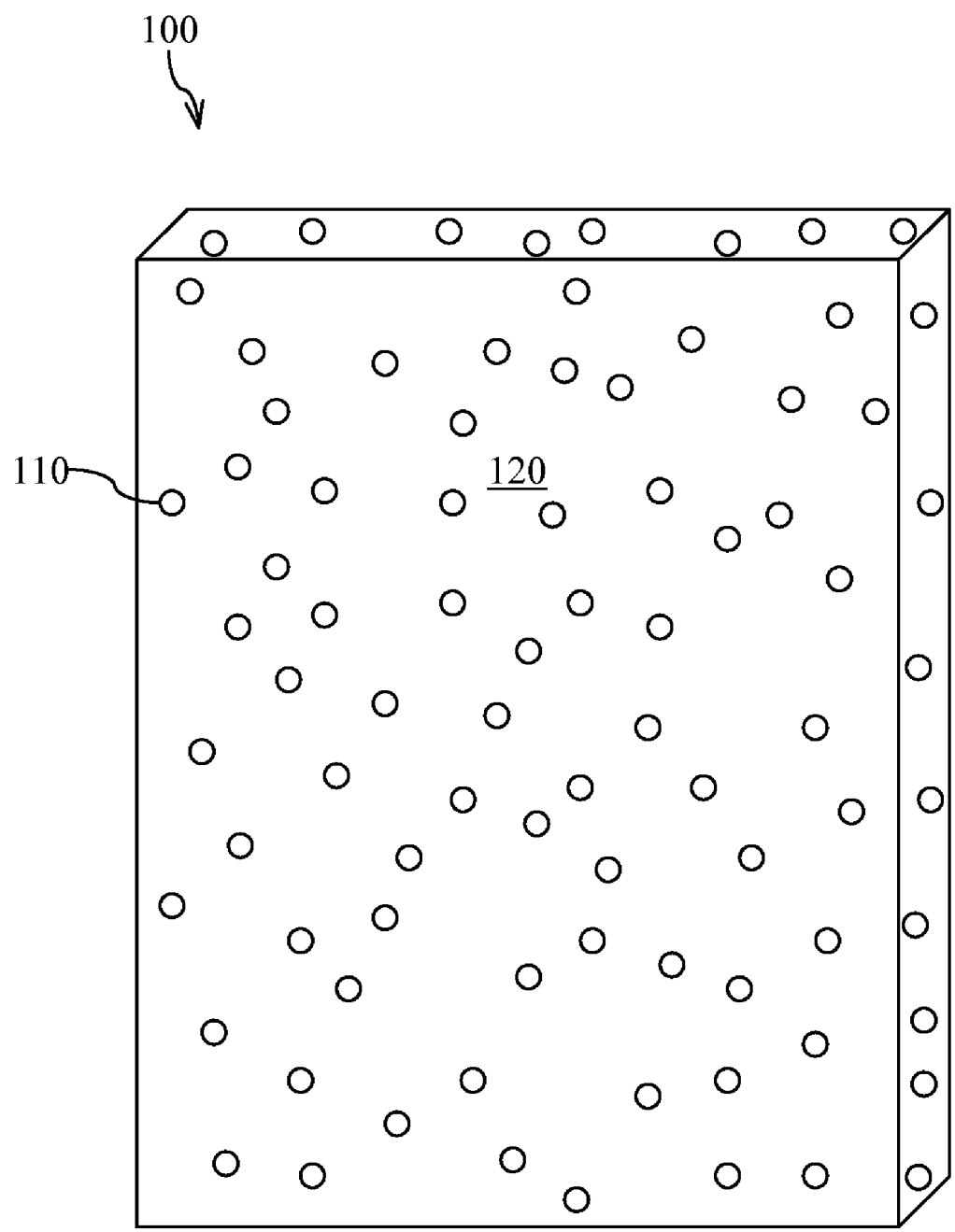
FIG. 1 is a schematic illustration of a perspective view of one of a plurality of samples according to a first embodiment.
Figure 2:
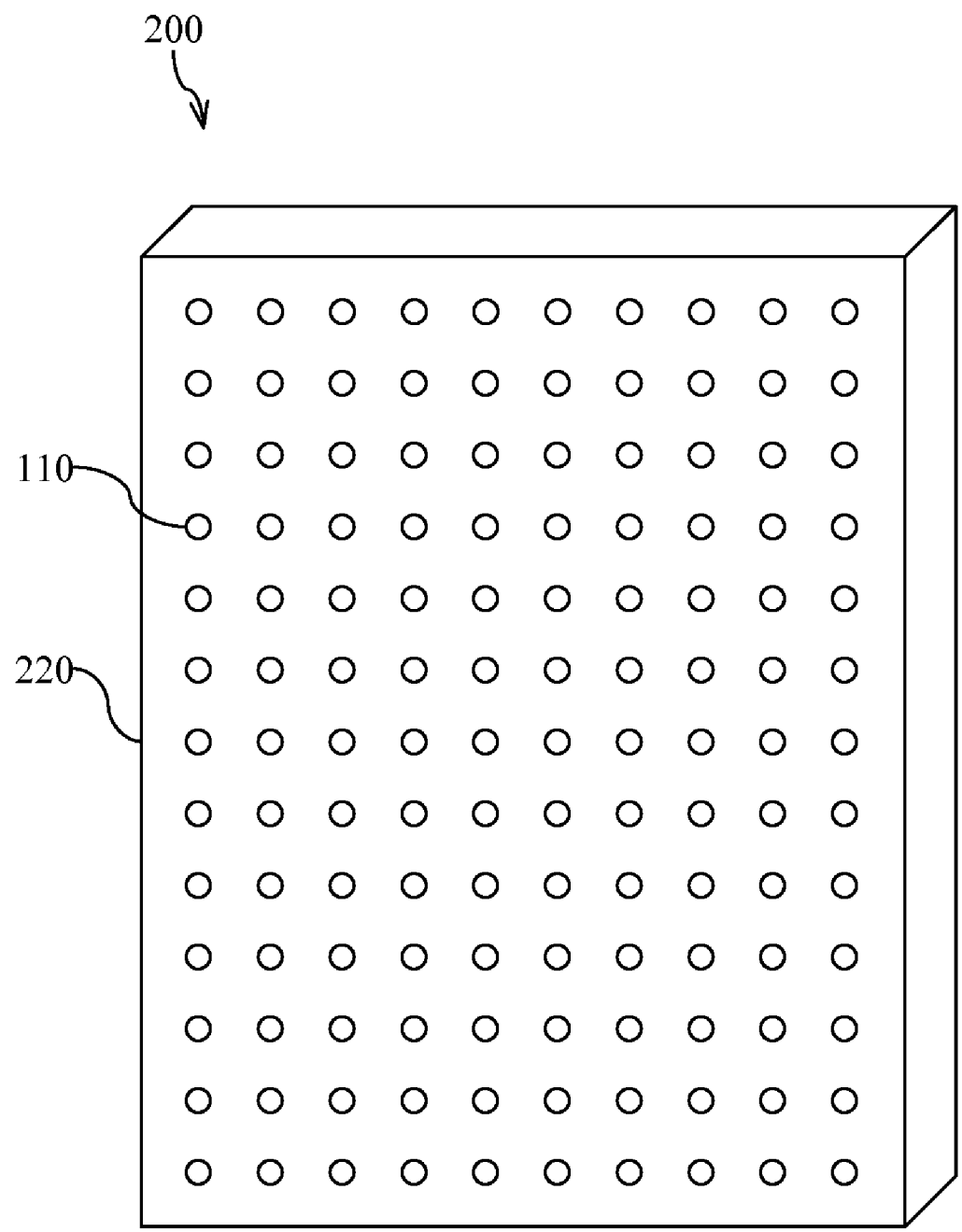
FIG. 2 is a schematic illustration of a perspective view of one of a plurality of samples according to a second embodiment.

With reference to FIGS. 1 and 2, the present invention provides a plurality of samples for selecting a target sample 100 or 200 from the plurality of samples. Each sample 100 or 200 of the plurality of samples includes particles 110 dispersed in a carrier 120 or 220. The plurality of samples is designed as a set of particle standards for assessment of the measurement accuracy or the detection sensitivity of an optical particle analyzer as a value of an optical property of the particles 110 approaches that of the carrier 120 or 220. Preferably, the plurality of samples consists of at least 5 samples 100 or 200.

The particles 110 in each sample 100 or 200 have a predetermined particle dimension. Typically, the particles 110 are spherical or circular, and the predetermined particle dimension is particle diameter. However, the particles 110 may have any desired shape with a measurable particle dimension. For example, the predetermined particle dimension may be the particle equivalent circular diameter (ECD), the particle Feret diameter, the particle Feret length, the particle Feret width, the particle aspect ratio, the particle circularity, the particle absorption intensity, or any other particle dimension measurable by conventional particle-morphology algorithms. Typically, the predetermined particle dimension is between 0.1 μm and 10 mm. Preferably, the predetermined particle dimension is between 0.5 μm and 30 μm. It is also preferable that the predetermined particle dimension be traceable to standards provided by the National Institute of Standards and Technology (NIST) or by some other independent body.

The particles 110 in each sample 100 or 200 are substantially uniform in size and shape. That is, all the particles 110 in each sample 100 or 200 have the predetermined particle dimension, within narrow predetermined limits. Typically, the coefficient of variation from the predetermined particle dimension is less than 10%. Preferably, the coefficient of variation is less than 5%. Furthermore, the predetermined particle dimension is the same for each sample 100 or 200.

The particles 110 in each sample 100 or 200 may be composed of a variety of materials. Importantly, the material selected for the particles 110 must be stable, inert, and dispersible in the carrier 120 or 220. In most instances, the particles 110 are solid; however, the particles 110 may also be hollow or filled with a liquid. Preferably, the particles 110 include a polymer, such as polystyrene or Teflon, a glass, such as fused silica or a compound glass, or a metal, such as gold, as a major component. In some instances, a light-absorbing agent, such as a dye or a transition-metal compound, or a coating, such as an antireflection coating or a fluorescent layer, is also included in the particles 110 to modify a value of an optical property of the particles 110. Furthermore, surfaces of the particles 110 may be modified to facilitate dispersion in the carrier 120 or 220.

In each sample 100 or 200, the particles 110 are dispersed in a carrier 120 or 220 at a predetermined particle concentration, which falls within the specified particle concentration range of the optical particle analyzer. Typically, the predetermined particle concentration is between 1000 particles/mL and 10 000 000 particles/mL; however, the predetermined particle concentration may also be lower than 1000 particles/mL. The predetermined particle concentration is the same for each sample 100 or 200.

Similarly to the particles 110, the carrier 120 or 220 in each sample 100 or 200 may be composed of a variety of materials. Importantly, the material selected for the carrier 120 or 220 must be stable and inert towards the particles 110, as well as amenable to dispersion of the particles 110 therein.

According to a first embodiment of the plurality of samples, each sample 100 includes particles 110 suspended in a fluid, which serves as the carrier 120, as illustrated in FIG. 1. Preferably, the fluid includes one or more liquids as major components. Examples of suitable liquids include water, alcohols, such as ethylene glycol, and other common solvents. In addition, the fluid may also include one or more dissolved solids to modify a value of an optical property of the carrier 120, to improve the stability of the carrier 120, to inhibit microbial growth in the carrier 120, and/or to facilitate suspension of the particles 110 in the carrier 120. Examples of suitable solids include sugars, salts, and other common solutes. In some instances, a light-absorbing agent, such as a dye or a transition-metal compound, is included in the fluid. If necessary, a surfactant, a viscosity modifier, a buffer, a preservative, or another type of additive may also be included in the fluid. Preferably, the fluid is a solution or a colloid.

According to a second embodiment of the plurality of samples, each sample 200 includes particles 110 dispersed in a solid plate, which serves as the carrier 220, as illustrated in FIG. 2. The particles 110 are disposed in a two-dimensional array parallel to a surface of the solid plate. Preferably, the two-dimensional array is regular. Preferably, the solid plate includes a polymer, such as polystyrene or Teflon, or a glass, such as fused silica or a compound glass, as a major component. In some instances, a light-absorbing agent, such as a dye or a transition-metal compound, or a coating, such as an antireflection coating, is also included in the solid plate to modify a value of an optical property of the carrier 220.

According to either embodiment of the plurality of samples, each sample 100 or 200 has a predetermined ratio of a value of an optical property of the particles 110 to a value of the same optical property of the carrier 120 or 220, at a wavelength of operation of the optical particle analyzer. Preferably, the optical property is refractive index or a transmission property, such as transmission coefficient, absorption coefficient, or attenuation coefficient. Preferably, the predetermined ratio is within ±15% of 1 for each sample 100 or 200.

Ideally, the values of the optical property of the particles 110 and the carrier 120 or 220 in each sample 100 or 200 are similar to those of particles and carriers encountered in samples under study for a particular application. For example, in instances when the optical particle analyzer is to be used for life-science applications, it is preferred that the value of the optical property of the particles 110 is within a range of values of the optical property of biological particles and that the value of the optical property of the carrier 120 or 220 is within a range of values of the optical property of water-based carriers. Thus, in such instances, the values of refractive index of the particles 110 and the carrier 120 or 220 in each sample 100 or 200 are, typically, between 1.3 and 1.7 at 589 nm.

An important feature of the present invention is that the predetermined ratio of the value of the optical property of the particles 110 to the value of the same optical property of the carrier 120 or 220 is different for each sample 100 or 200. In effect, the plurality of samples is a series of samples, within which the predetermined ratio approaches 1 for successive samples 100 or 200. Preferably, the predetermined ratio differs by a regular interval for successive samples 100 or 200 in the series of samples.

In some instances, the value of the optical property of the particles 110 is the same for each sample 100 or 200, whereas the value of the optical property of the carrier 120 or 220 is different for each sample 100 or 200. In such instances, the value of the optical property of the carrier 120 or 220 is varied by modifying a composition or a structure, such as the nanostructure or the microstructure, of the carrier 120 or 220. For example, when the carrier 120 is a fluid including a liquid, the value of refractive index of the carrier 120 can be varied by adding a second liquid or a solid to the fluid in different concentrations, or the value of a transmission property of the carrier 120 can be varied by adding a light-absorbing agent to the fluid in different concentrations. For another example, when the carrier 220 is a solid plate including a polymer, the value of refractive index of the carrier 220 can be varied by modifying the concentration of a monomer in a copolymer, or the value of a transmission property of the carrier 220 can be varied by adding a light-absorbing agent or a coating to the solid plate in different concentrations or thicknesses, respectively.

In other instances, the value of the optical property of the particles 110 is different for each sample 100 or 200, whereas the value of the optical property of the carrier 120 or 220 is the same for each sample 100 or 200. The value of the optical property of the particles 110 is varied by modifying a composition or a structure, such as the nanostructure or the microstructure, of the particles 110. For example, when the particles 110 include a glass, the value of refractive index of the particles 110 can be varied by modifying the concentration of a compound in a compound glass, or the value of a transmission property of the particles 110 can be varied by adding a light-absorbing agent or a coating to the particles 110 in different concentrations or thicknesses, respectively.

In an alternative embodiment, each sample 100 or 200 also has a second predetermined ratio of a value of a second optical property of the particles 110 to a value of the same second optical property of the carrier 120 or 220. Preferably, the second optical property is refractive index or a transmission property, such as transmission coefficient, absorption coefficient, or attenuation coefficient. Preferably, the second predetermined ratio is within ±15% of 1 for each sample 100 or 200. Ideally, the values of the second optical property of the particles 110 and the carrier 120 or 220 in each sample 100 or 200 are similar to those of particles and carriers encountered in samples under study for a particular application.

In some instances, the second predetermined ratio is the same for each sample 100 or 200, such that the plurality of samples forms a column of a matrix of the predetermined ratio by the second predetermined ratio. In other instances, the second predetermined ratio is different for each sample 100 or 200, such that the plurality of samples forms a diagonal of the matrix. In such instances, the value of the second optical property of either the particles 110 or the carrier 120 or 220 is varied by modifying a composition or a structure of the particles 110 or of the carrier 120 or 220, respectively, as described heretofore.

The present invention also provides a method for selecting a target sample 100 or 200 from the plurality of samples. According to the method, the plurality of samples is provided and is used to assess the measurement accuracy or the detection sensitivity of an optical particle analyzer as the value of the optical property of the particles 110 approaches that of the carrier 120 or 220, that is, as the predetermined ratio approaches 1.

To assess the measurement accuracy of the optical particle analyzer, the particle dimension of each sample 100 or 200 is measured with the optical particle analyzer to provide a measured particle dimension for each sample 100 or 200. Preferably, samples 100 or 200 having predetermined ratios approaching 1 are measured successively. The measured particle dimension is compared to the predetermined particle dimension to determine a measurement accuracy for each sample 100 or 200. The target sample 100 or 200 for which the predetermined ratio is closest to 1 and for which the measurement accuracy is equal to or better than a desired measurement accuracy is selected. The desired measurement accuracy is chosen to meet the requirements of a particular application and is, typically, better than ±5%.

Similarly, to assess the detection sensitivity of the optical particle analyzer, the particle concentration of each sample 100 or 200 is measured with the optical particle analyzer to provide a measured particle concentration for each sample 100 or 200. Preferably, samples 100 or 200 having predetermined ratios approaching 1 are measured successively. The measured particle concentration is compared to the predetermined particle concentration to determine a detection sensitivity for each sample 100 or 200. The target sample 100 or 200 for which the predetermined ratio is closest to 1 and for which the detection sensitivity is equal to or better than a desired detection sensitivity is selected. The desired detection sensitivity is chosen to meet the requirements of a particular application and is, typically, better than ±5%.

In an alternative embodiment, when each sample 100 or 200 has a second predetermined ratio, and when the second predetermined ratio is different for each sample 100 or 200, the target sample 100 or 200 for which the predetermined ratio is closest to 1, for which the second predetermined ratio is closest to 1, and for which the measurement accuracy or the detection sensitivity is equal to or better than the desired measurement accuracy or the desired detection sensitivity, respectively, is selected.

In another alternative embodiment, the measurement accuracy and the detection sensitivity of the optical particle analyzer are assessed simultaneously. The particle dimension and the particle concentration of each sample 100 or 200 are measured with the optical particle analyzer to provide a measured particle dimension and a measured particle concentration, respectively, for each sample 100 or 200. Preferably, samples 100 or 200 having predetermined ratios approaching 1 are measured successively. The measured particle dimension is compared to the predetermined particle dimension and the measured particle concentration is compared to the predetermined particle concentration to determine a measurement accuracy and a detection sensitivity, respectively, for each sample 100 or 200. The target sample 100 or 200 for which the predetermined ratio is closest to 1 and for which the measurement accuracy and the detection sensitivity are equal to or better than the desired measurement accuracy and the desired detection sensitivity, respectively, is selected.

To demonstrate the method, 13 samples 100 were provided, each of which included particles 110 composed of modified fused silica (refractive index 1.43 at 589 nm) in a carrier 120 composed of water (refractive index 1.33 at 589 nm) and/or ethylene glycol (refractive index 1.43 at 589 nm). The particles 110 had a predetermined particle diameter of 4.80 μm, with a coefficient of variation of less than 10%, and were dispersed in the carrier 120 at a concentration of 11 000 particles/mL. The value of refractive index of the carrier 120 was varied from 1.33 to 1.43 at 589 nm by varying the concentration of ethylene glycol in the carrier 120 from 0% to 100% by volume. Thus, each sample 100 had a different predetermined ratio of the value of refractive index of the particles 110 to that of the carrier 120, the predetermined ratio ranging from 1.08 to 1.

Figure 3:
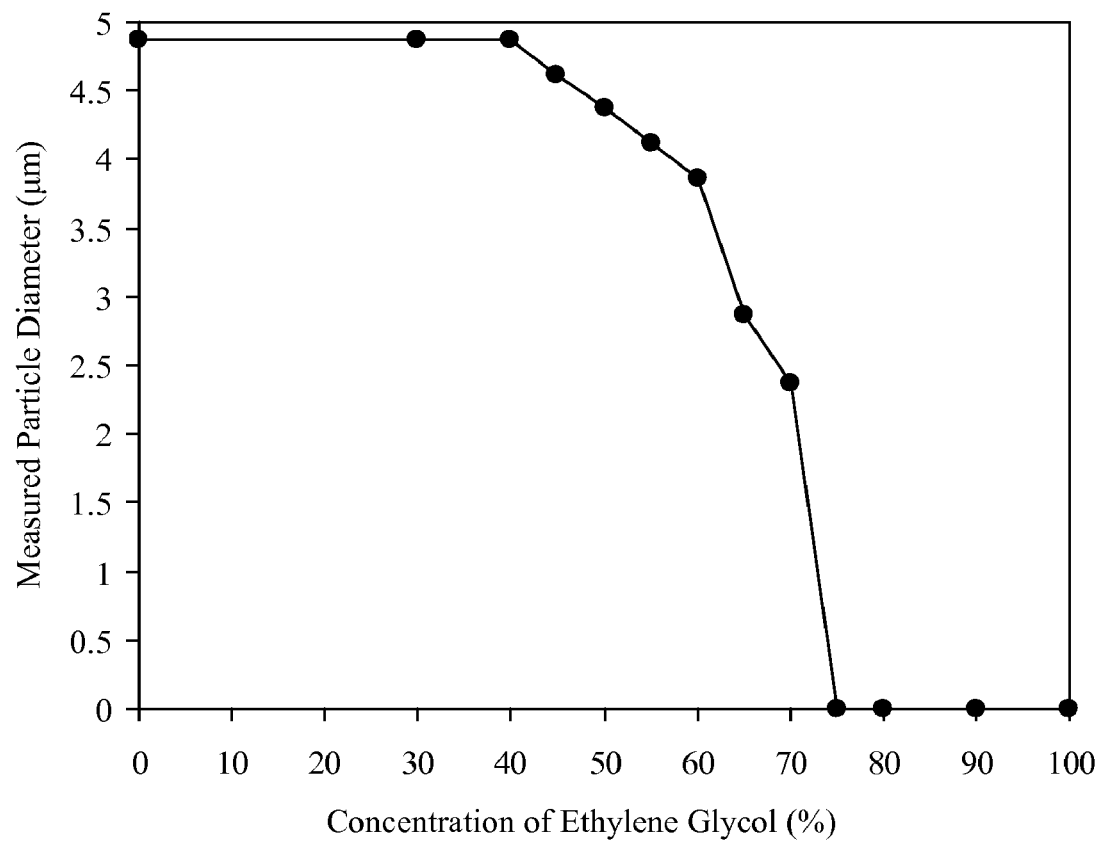
FIG. 3 is a plot of measured particle diameter as a function of concentration of ethylene glycol for a plurality of samples, as measured with a micro-flow imaging (MFI) particle analyzer.

To assess the measurement accuracy of a micro-flow imaging (MFI) particle analyzer, the particle diameter of each sample 100 was measured with the MFI particle analyzer. In FIG. 3, measured particle diameter is plotted as a function of concentration of ethylene glycol. The measured particle diameter for the sample 100 with a concentration of ethylene glycol of 0% was 4.87 μm, which corresponds to a measurement accuracy of 1.5% when compared with the predetermined particle diameter. For samples 100 with concentrations of ethylene glycol greater than 40%, the measured particle diameter decreased to 2.37 μm, which corresponds to a measurement accuracy of −51%, with increasing concentration of ethylene glycol up to 70%. For samples 100 with concentrations of ethylene glycol greater than 70%, the measured particle diameter was 0 μm, because the particles 110 were no longer detected.

For a desired measurement accuracy of ±2%, a measurement accuracy equal to or better than the desired measurement accuracy is only achieved for the samples 100 with concentrations of ethylene glycol less than 40%, that is, with predetermined ratios of the value of refractive index of the particles 110 to that of the carrier 120 of greater than 1.04. Thus, the sample 100 with a concentration of ethylene glycol of 40%, for which the predetermined ratio was closest to 1, was selected as the target sample 100.

As mentioned heretofore, such an assessment of the measurement accuracy or the detection sensitivity of an optical particle analyzer permits minimum instrument specifications to be established, instrument performance to be compared, standardized, and verified, and advances in instrument technology, such as phase contrast techniques, differential interference contrast techniques, noise-reduction hardware and software, and illumination techniques, to be quantified.

Figure 4:
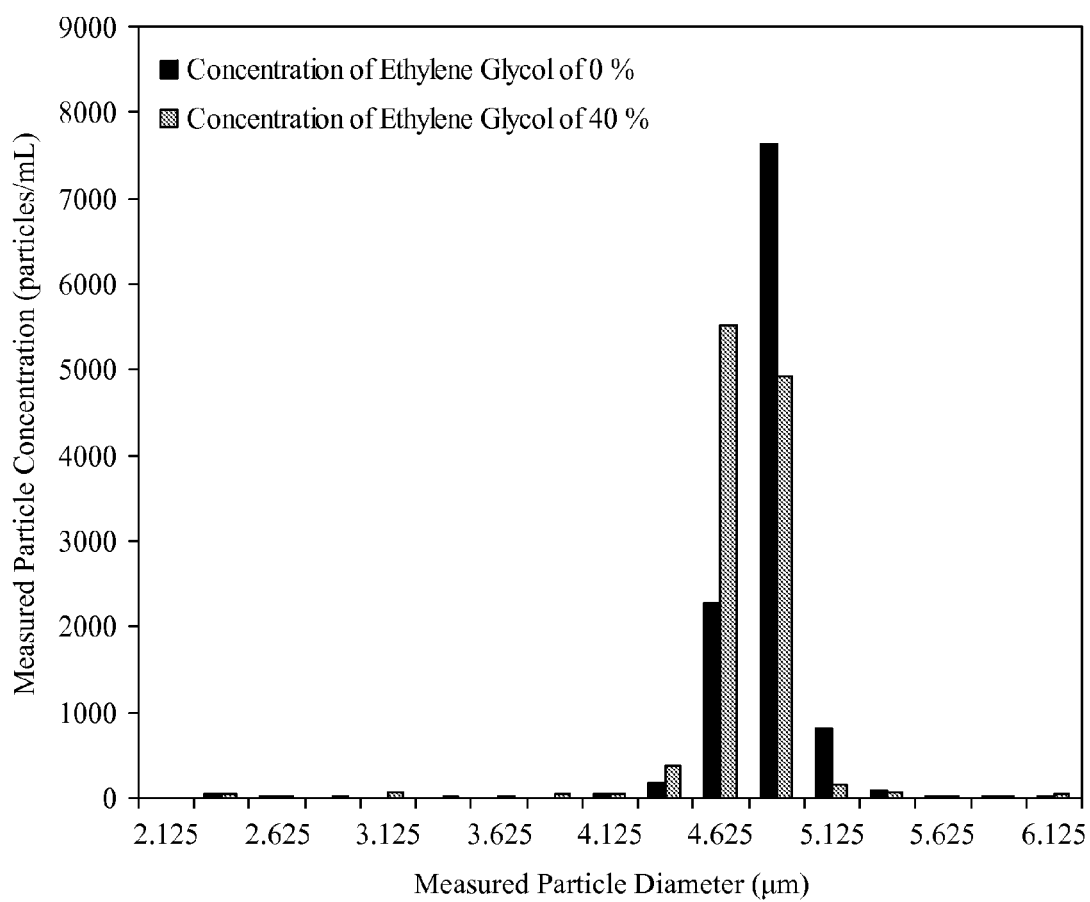
FIG. 4 is a plot of measured particle concentration as a function of measured particle diameter for samples with concentrations of ethylene glycol of 0% and 40%, as measured with the MFI particle analyzer.
Figure 5:
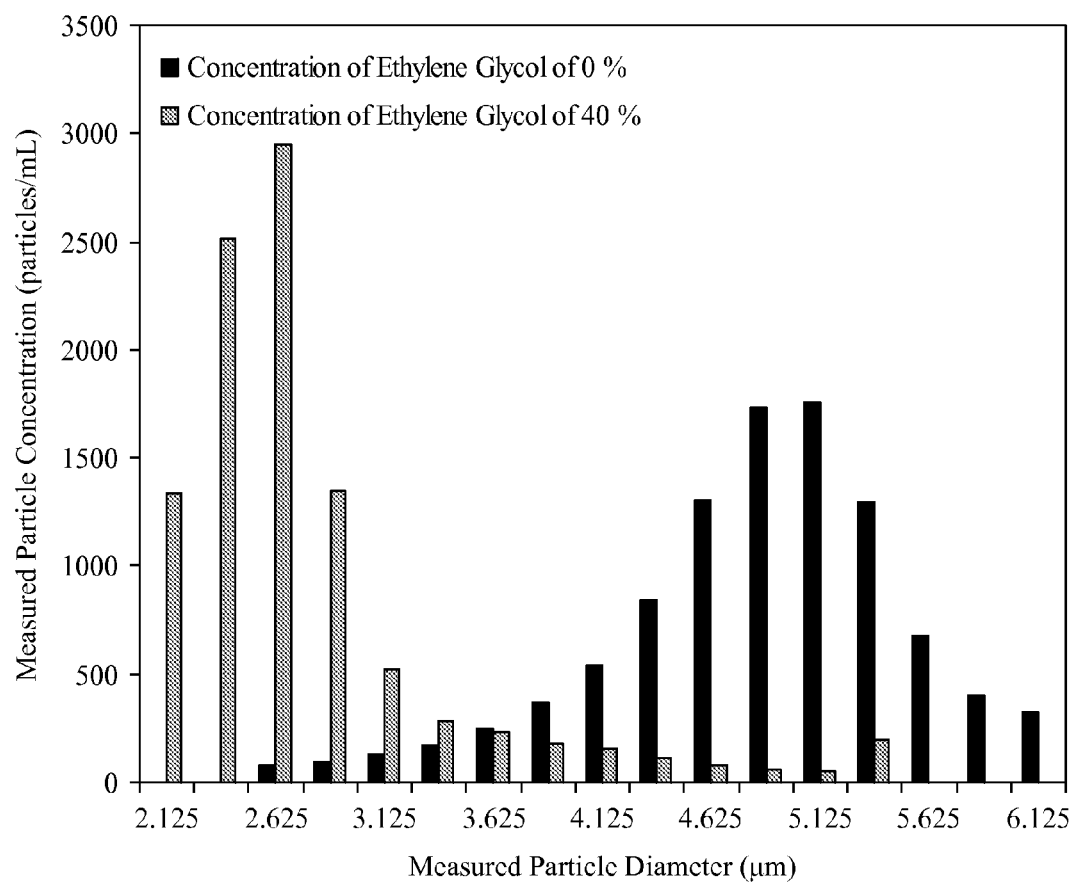
FIG. 5 is a plot of measured particle concentration as a function of measured particle diameter for samples with concentrations of ethylene glycol of 0% and 40%, as measured with a light-obscuration particle analyzer.

For example, the target sample 100 selected from the plurality of samples according to the first method was used to compare the instrument performance, in terms of measurement accuracy, of the MFI particle analyzer to that of a light-obscuration particle analyzer. The sample 100 with a concentration of ethylene glycol of 0% and the target sample 100 with a concentration of ethylene glycol of 40% were measured with both optical particle analyzers. In FIGS. 4 and 5, measured particle concentration is plotted as a function of measured particle size for the two samples 100, as measured with the MFI particle analyzer and with the light-obscuration particle analyzer, respectively. The measurement accuracies of both optical particle analyzers meet the desired measurement accuracy of ±2% for the sample 100 with a concentration of ethylene glycol of 0%. However, only the measurement accuracy of the MFI particle analyzer meets the desired measurement accuracy of ±2% for the target sample 100 with a concentration of ethylene glycol of 40%. Thus, the instrument performance, in terms of measurement accuracy, of the MFI particle analyzer is superior to that of the light-obscuration particle analyzer for samples 100 in which the particles 110 and the carrier 120 have similar values of refractive index.

Of course, numerous other embodiments of the present invention may be envisaged without departing from the spirit and scope of the invention.

We claim:

1. A plurality of samples for selecting a target sample from the plurality of samples, each sample comprising:
   a carrier; and
   particles of a predetermined particle dimension, within narrow predetermined limits, dispersed in the carrier at a predetermined particle concentration;
   wherein the predetermined particle dimension and the predetermined particle concentration are the same for each sample;
   wherein each sample has a first predetermined ratio of a value of a first optical property of the particles to a value of the same first optical property of the carrier;
   wherein the first predetermined ratio is different for each sample;
   wherein each sample has a second predetermined ratio of a value of a second optical property of the particles to a value of the same second optical property of the carrier; and
   wherein the second predetermined ratio is different for each sample.

2. The plurality of samples of claim 1, wherein the plurality of samples consists of at least 5 samples.

3. The plurality of samples of claim 1, wherein the particles are spherical or circular, and wherein the predetermined particle dimension is particle diameter.

4. The plurality of samples of claim 1, wherein the carrier is a fluid, and wherein the particles are suspended in the fluid.

5. The plurality of samples of claim 1, wherein the carrier is a solid plate, and wherein the particles are disposed in a two-dimensional array parallel to a surface of the solid plate.

6. The plurality of samples of claim 5, wherein the two-dimensional array is regular.

7. The plurality of samples of claim 1, wherein the first optical property is refractive index.

8. The plurality of samples of claim 1, wherein the first optical property is a transmission property.

9. The plurality of samples of claim 8, wherein the transmission property is transmission coefficient, absorption coefficient, or attenuance coefficient.

10. The plurality of samples of claim 1, wherein the first predetermined ratio is within ±15% of 1 for each sample.

11. The plurality of samples of claim 1, wherein the value of the first optical property of the particles is within a range of values of the same first optical property of biological particles, and wherein the value of the first optical property of the carrier is within a range of values of the same first optical property of water-based carriers.

12. The plurality of samples of claim 1, wherein the plurality of samples is a series of samples, and wherein the first predetermined ratio approaches 1 for successive samples in the series of samples.

13. The plurality of samples of claim 12, wherein the first predetermined ratio differs by a regular interval for successive samples in the series of samples.

14. The plurality of samples of claim 1, wherein the value of the first optical property of the particles is the same for each sample, wherein the value of the first optical property of the carrier is different for each sample, and
- wherein the value of the first optical property of the carrier is varied by modifying a composition or a structure of the carrier.

15. The plurality of samples of claim 1, wherein the value of the first optical property of the particles is different for each sample, wherein the value of the first optical property of the carrier is the same for each sample, and wherein the value of the first optical property of the particles is varied by modifying a composition or a structure of the particles.

16. A plurality of samples for selecting a target sample from the plurality of samples, each sample comprising:
- a carrier; and
- particles of a predetermined particle dimension, within narrow predetermined limits, dispersed in the carrier at a predetermined particle concentration;
- wherein the predetermined particle dimension and the predetermined particle concentration are the same for each sample;
- wherein each sample has a first predetermined ratio of a value of a first optical property of the particles to a value of the same first optical property of the carrier;
- wherein the first predetermined ratio is different for each sample;
- wherein each sample has a second predetermined ratio of a value of a second optical property of the particles to a value of the same second optical property of the carrier; and
- wherein the second predetermined ratio is the same for each sample.

17. A method for selecting a target sample from a plurality of samples with an optical particle analyzer, comprising:
- providing the plurality of samples;
- wherein each sample comprises a carrier, and particles of a predetermined particle dimension, within narrow predetermined limits, dispersed in the carrier at a predetermined particle concentration;
- wherein the predetermined particle dimension and the predetermined particle concentration are the same for each sample;
- wherein each sample has a first predetermined ratio of a value of a first optical property of the particles to a value of the same first optical property of the carrier;
- wherein the first predetermined ratio is different for each sample;
- wherein each sample has a second predetermined ratio of a value of a second optical property of the particles to a value of the same second optical property of the carrier; and
- wherein the second predetermined ratio is different for each sample;
- measuring the particle dimension or the particle concentration of each sample with the optical particle analyzer to provide a measured particle dimension or a measured particle concentration, respectively, for each sample;
- comparing the measured particle dimension to the predetermined particle dimension or the measured particle concentration to the predetermined particle concentration to determine a measurement accuracy or a detection sensitivity, respectively, for each sample; and
- selecting the target sample for which the first predetermined ratio is closest to 1, for which the second predetermined ratio is closest to 1, and for which the measurement accuracy or the detection sensitivity is equal to or better than a desired measurement accuracy or a desired detection sensitivity, respectively.

18. The method of claim 17, wherein the particle dimension and the particle concentration of each sample are measured with the optical particle analyzer to provide a measured particle dimension and a measured particle concentration, respectively, for each sample; wherein the measured particle dimension is compared to the predetermined particle dimension and the measured particle concentration is compared to the predetermined particle concentration to determine a measurement accuracy and a detection sensitivity, respectively, for each sample; and wherein the target sample for which the first predetermined ratio is closest to 1, for which the second predetermined ratio is closest to 1, and for which the measurement accuracy and the detection sensitivity are equal to or better than a desired measurement accuracy and a desired detection sensitivity, respectively, is selected.

* * * * *